United States Patent

Merriman et al.

[11] Patent Number: 5,972,963
[45] Date of Patent: Oct. 26, 1999

[54] 3-ARYL-2-(1-SUBSTITUTED 4-PIPERIDINYL)-1,1-DIOXO-3H-BENZO[D] ISOTHIAZOLES AND RELATED COMPOUNDS

[75] Inventors: Gregory H. Merriman, Phillipsburg; Barbara S. Rauckman, Flemington, both of N.J.

[73] Assignee: Hoechst Marion Roussel, Inc., Bridgewater, N.J.

[21] Appl. No.: 08/993,928

[22] Filed: Dec. 18, 1997

Related U.S. Application Data

[60] Provisional application No. 60/109,800, Dec. 23, 1996.

[51] Int. Cl.$^6$ .................. A61K 31/445; C07D 417/04
[52] U.S. Cl. ................................... 514/321; 546/198
[58] Field of Search .................. 546/198; 514/321

[56] References Cited

PUBLICATIONS

J. Szabo et al., Tetrahedron vol. 45, No. 9, pp. 2731–2736 (1989).
P. Feit, et al., J. of Med. Chem., vol. 16, No. 2, pp. 127–130 (1973).
H. Watanabe, et al., J. Org. Chem., vol. 33, No. 2, pp. 900–903 (1968).

*Primary Examiner*—Patricia L. Morris
*Attorney, Agent, or Firm*—Frommer Lawrence & Haug LLP

[57] ABSTRACT

This invention relates to 3-aryl-2-(1-substituted-4-piperidinyl)-1,1-dioxo-3H-benzo[d]isothiazoles and related compounds of the formula,

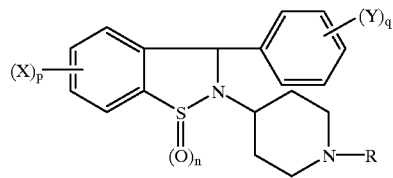

where X and Y are independently halogen, loweralkyl, loweralkoxy, arylloweralkoxy, acyl, hydroxy, nitro, amino, trifluoromethyl and hydrogen; n, p and q are independently integers of 1 or 2; R is hydrogen, loweralkyl, arylloweralkyl, acyl, —$(CH_2)_m$—$OR_1$,—$(CH_2)NHR_1$,

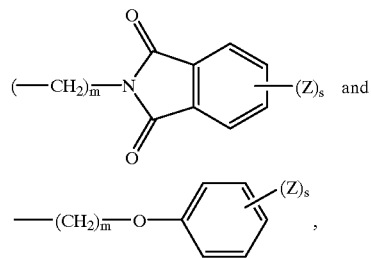

where $R_1$ is hydrogen, loweralkyl, arylloweralkyl, acyl and loweralkoxycarbonyl; Z is hydrogen, halogen, loweralkyl, loweralkoxy and acyl; m is an integer of 2 to 4; is an integer of 1 or 2; and the pharmaceutically acceptable acid addition salts thereof and the optical isomers thereof where such isomers exist.

48 Claims, No Drawings

3-ARYL-2-(1-SUBSTITUTED 4-PIPERIDINYL)-1,1-DIOXO-3H-BENZO[D] ISOTHIAZOLES AND RELATED COMPOUNDS

This application claims the benefit of Provisional Application 60/109,800, filed Dec. 23, 1996.

To the best of our knowledge, the compounds of the present invention have not heretofore been described or suggested.

The compounds of the present invention have the general formula

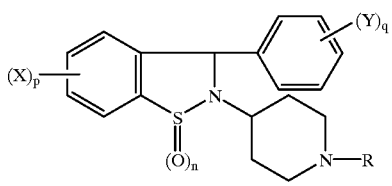

where X and Y are independently halogen, loweralkyl, loweralkoxy, aryloweralkoxy, acyl, hydroxy, nitro, loweralkyl, amino, trifluoromethyl, or hydrogen; n, p and q are independently integers of 1 or 2; R is hydrogen, alkyl, arylloweralkyl, acyl, —(CH$_2$)$_m$—OR$_1$,—(CH$_2$)NHR$_1$,

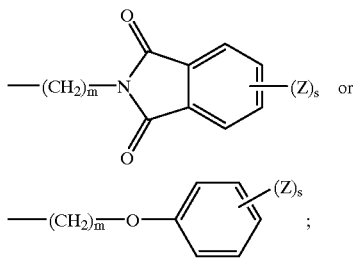

where R$_1$ is hydrogen, lowerlakyl, arylloweralkyl and acyl or loweralkoxycarbonyl; m is an integer of 2 to 4; Z is hydrogen, halogen, loweralkyl, loweralkoxy or acyl; s is an integer of 1 or 2; and the pharmaceutically acceptable acid addition salts thereof.

Throughout the specification and appended claims, a given chemical formula or name shall encompass all stereo isomers thereof where such isomers exist. In addition, this invention, shall encompass the bio-precursors of Compound I and the metabolites thereof. As used herein, the term "bio-precursors" shall mean a compound or compounds which when introduced, e.g. ingested into the body of a mammal, such as a man, are converted by biological action to Compound I. An example of but not a limitation to such a bio-precursor is the well known class of compounds known as pro-drugs.

In the above definitions the term "lower" means the group it is describing contains from 1 to 6 carbon atoms. The term "alkyl" refers to a straight or branched chain hydrocarbon containing no unsaturation, e.g. methyl, ethyl, isopropyl, 2-butyl, neopentyl, n-hexyl, etc.; the term "alkoxy" refers to a monovalent substituent which consists of an alkyl group linked through an ether oxygen having its free valence bond from the ether oxygen, e.g. methoxy, ethoxy, propoxy, butoxy, pentoxy, etc.; the term "aryl" refers to a phenyl group of the formula

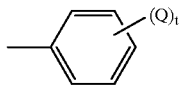

where Q and t are as defined below; the term "aryllower-alkyl" refers to a monovalent substituent which consists of an aryl group, e.g. phenyl, o-tolyl, m-methoxyphenyl, etc., linked through a lower alkylene group having its free valence bond from a carbon of the lower alkylene group and having the formula of

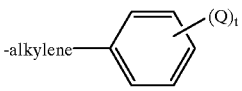

where Q is hydrogen, halogen, nitro, loweralkyl, loweralkoxy, loweracyl, CF$_3$, NH$_2$ and t is an integer of 1 to 3; the term "alkylene" refers to a bivalent radical of the lower branched or unbranched alkyl group it is derived from having valence bonds from two terminal carbons thereof, e.g. ethylene (—CH$_2$CH$_2$—), propylene (—CH$_2$CH$_2$CH$_2$—), isopropylene (—CH(CH$_3$)CH$_2$—), etc.; the term "acyl" refers to a substituent having the formula —C(=O)R$_2$ where R$_2$ is aryl or loweralkyl; and the term "halogen" refers to a member of the family consisting of fluorine, chlorine, bromine and iodine.

The compounds of the present invention are prepared in the following manner where the substituents R, R$_1$, X, Y, Z and the integers m, n, p, q, r and s are as defined earlier.

A compound of the formula, (II)

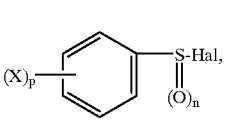

where Hal is a halogen, is selected. Such compounds II are well known and can be prepared generally in the manner described in (1) Voegel's Texbook of Practical Organic Chemistry 5th Ed., p. 877, Authors: B. S. Furniss, A. J. Hannaford, P. W. G. Smith, A. R. Tatchell. Compound II is reacted with an amine III of the formula, (III)

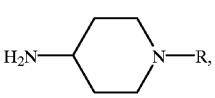

to form compound (IV), (IV)

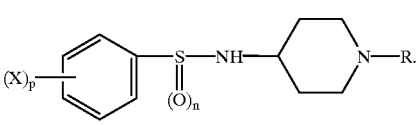

Compounds III are well known and can be prepared in a manner as described in Crider, A. M.; Floss, H. G.; Cassady, J. M.; Bradner, W. J.; J. Med. Chem. (1980), 23(8).848–51. Many are commercially available. The reaction between Compounds II and III to produce Compound IV is conducted under standard acylation reaction conditions. Typically, the reaction is conducted in the presence of a chlorinated hydrocarbon such as, for example, $CH_2Cl_2$, $CHCl_3$ or $ClCH_2CH_2Cl$ at a temperature of 20° to 40° C. for 1 to 5 hours to obtain Compound IV.

Compound IV is then metalated followed by condensation with an aldehyde of the formula,

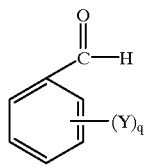
(V)

to form compound VI of the formula,

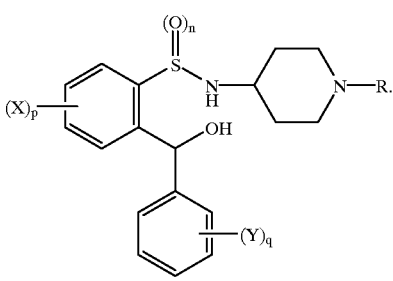
(VI)

Typically, compound IV is reacted with compound V in the presence of a suitable metalation reagent, e.g. n-butyllithium, s-butyllithium, t-butyllithium, etc., in an ethereal solvent, e.g. dimethoxyethane (DME), etc., at a temperature of 0° C. to 25° C., for 1 to 2 hours to form Compound VI.

Compound VI is subjected to a cyclodehydration reaction to form compound I of the invention. Typically, compound VI is treated with a conventional cyclodehydration agent selected from a mineral acid, such as conc. $H_2SO_4$, etc., a Mitsonobu reagent, such as, DEAD $PPH_3$, etc. in an ethereal solvent, e.g. THF, $Et_2O$, etc., for 1 to 2 hours to form compound I of the invention.

Where R is H in Compound (I), this compound can then be further reacted with a compound of the formula $R^1$—Hal (VII) where Hal is halogen and $R^1$ includes all the substituents of R except hydrogen, e.g. loweralkyl, etc. The reaction is typically conducted under conventional reaction conditions, such as in a dipolar aprotic solvent, e.g. DMF, DMSO, etc., at a temperature of 25 to 150° C. for 10 to 20 hours to form Compound I where R is $R^1$.

The compounds of Formula (I) of the present invention are useful as modulators of neurotransmitter function such as serotonergic and adrenergic, and as such are useful as antidepressants, and dopaminergic function, and as such may be useful for diseases where the potentiation of dopaminergic activity may be helpful, e.g.

Parkinson's Disease.

Three test protocols described below, namely, (1) inhibition of norepinephrin (NE) uptake;
(2) inhibition of serotonin (5HT) uptake; and
(3) inhibition of dopamine (DA) uptake, are used to ascertain the biological properties of the compounds of this invention. Following the descriptions of the protocols, results for some of the compounds of the invention are set forth in Table 1.

Inhibition of [$^3$H]-Norepinephrine Uptake in Rat Whole Brain or Hypothalamic Synaptosomes Purpose:

This assay is used as a biochemical screen for potential antidepressants which block norepinephrine uptake.

Introduction:

The neuronal re-uptake mechanism for norepinephrine (NE) is the most important physiological means for inactivating NE by removing the transmitter from the synaptic cleft (1). NE uptake is accomplished by a saturable, stereospecific, high-affinity ($K_m$–$10^{-7}$–$10^{-6}$ M), sodium dependent, active transport system, which has been shown to exist in both peripheral and central nervous system tissue, using slice, homogenate and purified synaptosome preparations (2). NE uptake is potently inhibited by cocaine, phenethylamines and tricyclic antidepressants (3). It is also inhibited by ouabain, metabolic inhibitors and phenoxybenzarrine. The inhibition of NE uptake by clinically effective tricyclic antidepressants is an important link in the catecholamine hypothesis of affective disorders (4). In this series of compounds, the secondary amines (e.g. desipramine) are more active than the tertiary amines (e.g. imipramine). Extensive structure activity relationships for NE uptake have been studied in the past.

There are large regional variations in NE uptake (7–9) which correlate with the endogenous levels of NE. The hypothalamus shows the highest level of NE and the greatest uptake. This region is used for further testing of compounds showing activity in whole brain preparations.

Synaptosomal [$^3$H]-NE uptake is a useful marker for the integrity of noreadrenergic neurons after lesioning experiments, as well as an assay for compounds which potentiate the action of NE by blocking the reuptake mechanism.

Procedure

A. Animals: Male CR Wistar rats (100–125 g).
B. Reagents—
1. Krebs-Henseleit Bicarbonate Buffer, pH 7.4 (KHBB): Make a 1 liter batch, containing the following salts.

|  | g/L | mM |
| --- | --- | --- |
| NaCl | 6.92 | 118.4 |
| KCl | 0.35 | 4.7 |
| $MgSO_4 7H_2O$ | 0.29 | 2.2 |
| $NHCO_3$ | 2.10 | 24.9 |
| $CaCl_2$ | 0.14 | 1.3 |
| Prior to use add: | | |
| Dextrose | 2 mg/ml | 11.1 mM |
| Iproniazid phosphate | 0.30 mg/ml | 0.1 mM |

Aerate for 60 minutes with 95% $O_2$/5% $CO_2$, check pH (7.4±0.1); then add bovine serum albumin (Sigma cat#A-7906) 1 mg/ml.

2. 0.32 M Sucrose: 21.9 g of sucrose, bring to 200 ml.

3. L(-)-Norepinephrine bitartrate is obtained from Sigma Chemical Co. A 0.1 mM stock solution is made up in 0.01 N HCl. This is used to dilute the specific activity of theradiolabeled NE.

4. Levo-[Ring-2,5,6-$^3$H]-Norepinephrine (40–50 Ci/mmol) is obtained from New England Nuclear.

The final desired concentration of [$^3$H]-NE in the assay is 50 nM. The dilution factor is 0.8. Therefore, the KHBB is made up to contain 62.5 nM [$^3$H]-NE.

Add to 100 ml of KHBB.

| A) 59.4 μl of 0.1 mM NE = | 59.4 nM |
|---|---|
| B) 0.31 moles of [³H]-NE = | 3.1 nM |
| | 55.5 nM |

*Calculate volume added from specific activity of [³H]-NE

5. For most assays, a 1 mM stock solution of the test compound is made up in a suitable solvent and serially diluted such that the final concentration in the assay ranges from $2 \times 10^{-8}$ to $2 \times 10^{-5}$ M. Seven concentrations are used for each assay. Higher or lower concentrations may be used depending on the potency of the compound.

C. Tissue Preparation

Male Wistar rats are decapitated and the brain rapidly removed. Either whole brain minus cerebella or hypothalamus is weighed and homogenized in 9 volumes of ice-cold 0.32 M sucrose using a Potter-Elvejhem homogenizer. Homogenization should be done with 4–5 up and down strokes at medium speeds to minimize synaptosome lysis. TH homogenate is centrifuged at 1000 g for 10 minutes at 0°–4° C. The supernatant ($S_1$) is decanted and is used for uptake experiments.

D. Assay

800 μl KHBB [³H]-NE
20 μl Vehicle or appropriate drug concentration
200 μl Tissue suspension Tubes are incubated at 37° C., under a 95% $O_2$/5% $CO_2$ atmosphere for 5 minutes. For each assay, 3 tubes are incubated with 20 μl of vehicle at 0° C. in a ice bath. After incubation all tubes are immediately centrifuged at 4000 g for 10 minutes. The supernatant fluid is aspirated and the pellets dissolved by adding 1 ml of solubilizaer (Triton X–100+50% EtOH, 1:4 v/v). The tubes are vigorously vortexed, decanted into scientillation vials, and counted in 10 ml of Liquiscint scintillation countering cocktail. Active uptake is the difference between cpm at 37° C. and 0C. The percent inhibition at each drug concentration is the mean of three determinations $IC_{50}$ values are derived from log-probit analysis.

References

1. Hertting. G. and Axelrod, J., "Fate of tritiated noradrenaline at the sympathetic nerve-endins" Nature 192: 172–173 (1961).
2. Paton, D. M., "Neuronal transport of norepinephrine and dopamines." Pharmacol. 21: 85–92 (1980).
3. Iversen, L. L., "Uptake mechanisms for neurotransmitter arnines." Biochem. Pharmacol. 23: 1927–1934 (1974).
4. Schildkraut, J. J. "The catecholamine hypothesis of affective disorders, a review of the supporting evidence." Am. J. Psychiat. 122: 509–522 (1965).
5. Horn, A. S., Coyle, J. T. and Snyder, S. H., "Catecholamine uptake by synaptosomes from rat brain: structure-activity relationship for drugs with differential effects in dopamine and norepinephrine neurons." Mol. Pharmacol. 7: 66–80 (1971).
6. Maxwell, R. A., Ferris, R. M., Burcsu, J., Woodward, E. C., Tang D. and Willard, K., "The phenyl rigns of tricyclic antidepressants and related compounds as determinants of the potency of inhibition of the amine pumps in adrenergic neurons of the rabbit aorta and in rat cortical synaptosomes." J. Pharmacol. Exp. Ther. 191: 418–430 (1974).
7. Glowinski, J. and Iversen, L. L., "Regional studies of catecholamines in rat brain." J. Neurochem. 13: 655–669 (1966).
8. Snyder, S. H. and Coyle, J. T., "Regional differences in [³H]-norepinephrine and [³H]-dopamine uptake into rat brain homogenates." J. Pharmacol. Exp. Ther. 165: 78–86 (1969).
9. Synder, S. H., Green, A. I. and Hendley. E. D., "Kinetics of [³H]-norepinephrine accumulations into slices from different regions of rat brain." J. Pharmacol. Exp. Ther. 164: 90–102 (1968).

Inhibition of [³H]-Serotonin Uptake in Rat Whole Brain Synaptosomes

Purpose

This assay is used a biochemical screen for compounds which block serotonin (5 HT) uptake, which may be useful as antidepressants and for the treatment of personality disorders such as obsessive compulsive disorder.

Asberg and co-workers have suggested that subjects with serotonergic hypofunction comprise a biochemical subgroup of depressed patients (1), while others (2) claim that altered serotonergic function determines the mood changes associated with affective disorders. Although the role of 5 HT in the etiology of depression is not clear; it is true that a number of antidepressant drugs block the 5 HT. reuptake S mechanism. In vitro receptor binding assays have shown that [³H]-imipramine labels 5 HT uptakes sites (10). Trazodone and zimelidine are clinically effective antidepressants (3) with fairly selective effects on 5 HT uptakes (4,5). More recently, fluoxetine has been shown to be both a selective and potent 5 HT uptake inhibitor.

[³H]-5 HT transport has been characterized in CNS tissue (6,7) and found to be saturable, sodium- and temperature-dependent, inhibited by ouabain, metabolic inhibitors, tryptarnine analogs (8) and tricyclic antidepressants (tertiary amines >>secondary amines) (9). The latter findings differentiate 5 HT uptake from catecholamine uptake. [³H]-5 HT uptake can also be used as a marker for serotonin nerve terminals.

Procedure

A. Animals: Male CR Wistar rats (100–125 g).
B. Reagents—
1. Krebs-Henseleit Bicarbonate Buffer, pH 7.4 (KHBB): Make a 1 liter batch, containing the following salts.

| | g/L | mM |
|---|---|---|
| NaCl | 6.92 | 118.4 |
| KCl | 0.35 | 4.7 |
| $MgSO_4 \cdot 7H_2O$ | 0.29 | 1.2 |
| $KH_2PO_4$ | 0.16 | 2.2 |
| $NaHCO_3$ | 2.10 | 24.9 |
| $CaCl_2$ | 0.14 | 1.3 |
| Prior to use add: | | |
| Dextrose | 2 mg/ml | 11.1 |
| Iproniazid phosphate | 0.30 mg/ml | 0.1 |

Aerate for 60 minutes with 95% $O_2$/5% $CO_2$, check pH (7.4±0.1).

2. 0.32 M Sucrose: 21.9 g of sucrose, bring to 200 ml.

3. Serotonin creatinine $SO_4$ is obtained from Sigma Chemical Co. A 0.1 mM stock solution is made up in 0.01 N HCl. This is used to dilute the specific activity of radiolabeled 5 HT.

4. 5-[1,2-³H(N)]-Hydroxytryptamine creatinine sulfate (Serotonin), specific activity 20–30 Ci/mmol is obtained from New England Nuclear.

The final desired concentration of ³H-5 HT in the assay is 50 nM. The dilution factor is 0.8. Therefore, the KHBB is made up to contain 62.5 nM [³H]-5 HT.

Add to 100 ml of KHBB.

| A) 56.1 µl of 0.1 mM 5HT = | 56.1nM |
|---|---|
| *B) 0.64 nmole of ³H-5Ht = | 6.4nM |
| | 62.5nM |

*Calculate volume added from specific activity of ³H-5HT

5. For most assays, a 1 mM solution of the test compound is made up in suitable solvent and serially diluted such that the final concentration in the assay ranges from $2\times10^{-8}$ to $2\times10^{-5}$ M. Seven concentrations are used for each assay. Higher or lower concentrations may be used depending on the potency of the compound.

C. Tissue Preparation

Male Wistar rats are decapitated and the brain rapidly removed. Whole brain minus cerebella is weighed and homogenized in 9 volumes of ice-cold 0.32 M sucrose using a Potter-Elvejhem homogenizer. Homogenization should be done with 4–5 up and down strokes at medium speeds to minimize synaptosome lysis. The homogenate is centrifuged at 1000 g for 10 minutes at 0°–4° C. The supernatant ($S_1$) is decanted and is used for uptake experiments.

D. Assay

800 µl KHBB +[³H]-5 HT.

20 µl Vehicle or appropriate drug concentration

200 µl Tissue suspension

Tubes are incubated at 37° C. under a 95% $O_2$/5% $CO_2$ atmosphere for 5 minutes. For each assay, 3 tubes are incubated with 20 µl of vehicle at 0° C. in an ice bath. After incubation all tubes are immediately centrifuged at 4000 g for 10 minutes. The supernatant fluid is aspirated and the pellets dissolved by adding 1 ml of solubilizer (Triton X–100+50% EtOH, 1:4 v/v). The tubes are vigorously vortexed, decanted into scintillation vials, and counted in 10 ml of Liquiscint scintillation counting cocktail. Active uptake is the difference between cpm at 37° C. and 0° C. The percent inhibition at each drug concentration is the mean of three determinations. $IC_{50}$ values are derived from log-probit analysis.

References

1. Asberg. M., Thoren, P., Traskman, L., Bertilsson, rger, V. Serotonin depression: A biochemical subgroup within the affective disorders. Science 191: 478–480 (1975).
2. DeMontigy, C. Enhancement of 5 HT neurotranstnission by antidepressant treatments J. Physiol. (Paris) 77: 455–461 (1980).
3. Feighner, J. P. Clinical efficacy of the newer antidepressants. J. Clin. Psychopharmacol, 1: 235–265 (1981).
4. Ogren, S. O., Ross, S. B., Hall, H., Holm, A. C. and Renyi, A. L. The pharmacology of zimelidine: A 5 HT selective reuptake inhibitor. Acta Psychiat. Scand. 290: 127–151 (1981).
5. Clements-Jewry, S., Robson, P. A. and Chidley, L. J. Biochemical investigations into the mode of action of trazodone. Neuropharmacol. 19: 1165–1173 (1980).
6. Ross, S. B. Neuronal transport of 5-hydroxytryptarnine. Pharmacol 21: 123–131 (1980). 7. Shaskan, E. G. and Snyder, S. H. Kinetics of serotomin accumulation into slices from rat brain: Relationship to catecholamine uptake. J. Pharmacol. Exp. Ther. 175: 404–418 (1970).
8. Horn, S. A. Structure-activity relations for the inhibition of 5 HT uptake into rat hypothalamic homogenates by serotonin and tryptamine analogues. J. Neurochem. 21: 883–888 (1973).
9. Horn, A. S. and Trace, R. C. A. M. Structure-activity relations for the inhibition of 5-hydroxytryptamine uptake by tricyclic antidepressant into synaptosomes from serrotonergic neurones in rat brain homogenates. Brit. J. Pharmacol. 51: 399–403 (1974).
10. Langer, S. Z., Moret, C., Raisman, R., Dubocovich, M. L. and Briley M. High affinity [³H]imipramine binding in rat hypothlamus: Association with uptake of serotonin but not norepinephrine. Science 210: 1133–1135 (1980).

Inhibition of ³H-Dopamine Uptake in Rat Striatal Synaptosomes

Purpose this assay is used to show differential drug effects on dopamine uptake versus nerepppinephrine uptake and to identify therapeutic agents for diseases where the potentiation of dopaminergic activity may be helpful (e.g. Parkinson's Disease).

Introduction

High-affinity, saturable, temperature and sodium-dependent transport of ³H-DA uptake is potently inhibited by cocaine, phenethylamines and ouabain, but, unlike NE, it is not potently inhibited by the tricyclic antidepressants (3). The only antidepressants which inhibit DA uptake are nomifensine (4) and bupropion (5). The relationship of DA uptake to the efficacy of these compounds is unknown. Coyle and Snyder (6) reported no stereo selectivity for the inhibition of DA uptake by d- or 1-amphetamine but conformational selectivity (gauche>anti) has been shown by other investigators (7).

Several authors have shown that at least part of the effect of ³H-amine accumulation by some compounds is due to direct releasing activity (4,8,9). However, there are some discrepancies in these reports. In order to differentiate the effects on uptake from the effects on release, the direct releasing effects must be determined in separate experiments. The most reliable method for determining neurotransmitter release is by a superfusion technique described by Raiteri et al. (10). This is a theoretical concern for studying the uptake of any substance in vitro, but is emphasized for dopamine uptake.

³H-DA uptake may also be used as a biochemical marker for dopaminergic nerve terminals, especially in conjunction with lesioning experiments.

Procedure

A. Animals: Male CR Wistar rats (100–125 g).

B. Reagents—

1. Krebs-Henseleit Bicarbonate Buffer, pH 7.4 (KHBB): Make a 1 liter batch containing the following salts:

| | g/L | mM |
|---|---|---|
| NaCl | 6.92 | 118.4 |
| KCl | 0.35 | 4.7 |
| $MgSO_4 \cdot 7H_2O$ | 0.29 | 1.2 |
| $KH_2PO_4$ | 0.16 | 2.2 |
| $NaHCO_3$ | 2.10 | 24.9 |
| $CaCl_2$ | 0.14 | 1.3 |
| Prior to use add: | | |
| Dextrose | 2 mg/ml | 11.1 |
| Iproniazid phosphate | 0.30 mg/ml | 0.1 |

Aerate for 60 minutes with 95% $O_2$/5% $CO_2$, check pH (7.4±0.1).

2. 0.32 M Sucrose: 21.9 g of sucrose, bring to 200 ml.

3. Dopamine HCl is obtained from Sigma Chemical Co. A 0.1 mM stock solution is made up in 0.01 N HCl. This is used to dilute the specific activity of radiolabeled 5 HT.

4. 3,4-[8-$^3$H(N)]-Dihydroxyphenylethylamine (Dopamine), specific activity 4–34 Ci/mmol is obtained from New England Nuclear.

The final desired concentration of $^3$H-DA in the assay is 50 nM. The dilution factor is 0.9. Therefore, the KHBB is made up to contain 55.5 nM [$^3$H]-5 DA.

Add to 100 ml of KHBB.

| | |
|---|---|
| A) 50 μl of 0.1 mM DA = | 50 nM |
| *B) 0.55 nmoles of $^3$HDA = | 5.5 nM |
| | 55.5 nM |

*Calculate volume added from specific activity of $^3$H-5DA

5. For most assays, a 1 mM stock solution of the test compound is made up in a suitable solvent and serially diluted such that the final concentration in the assay ranges from $2\times10^{-8}$ to $2\times10^{-5}$ M. Seven concentrations are used for each assay. Higher or lower concentrations may be used depending on the potency of the compound.

C. Tissue Preparation

Male Wistar rats are decapitated and the brain rapidly removed. Corpora striata are rapidly removed, weighed and homogenized in 9 volumes of ice-cold 0.32 M sucrose using a Potter-Elvejhem homogenizer. Homogenization should be done with 4–5 up and down strokes at medium speeds to minimize synaptosome lysis. The homogenate is centrifuged at 1000 g for 10 minutes at 0°–4° C. The supernatant (S) is decanted and is used for uptake experiments.

D. Assay

900 μl KHBB +[$^3$H]-DA.

20 μl Vehicle or appropriate drug concentration

100 μl Tissue suspension

Tubes are incubated at 37° C. under a 95% $O_2$/5% $CO_2$ atmosphere for 5 minutes. For each assay, 3 tubes are incubated with 20 μl of vehicle at 0° C. in an ice bath. After incubation all tubes are immediately centrifuged at 4000 g for 10 minutes. The supernatant fluid is aspirated and the pellets dissolved by adding 1 ml of solubilizer (Triton X-100+50% EtOH, 1:4 v/v). The tubes are vigorously vortexed, decanted into scintillation vials, and counted in 10 ml of Liquiscint scintillation counting cocktail. Active uptake is the difference between cpm at 37° C. and 0° C. The percent inhibition at each drug concentration is the mean of three determinations. $IC_{50}$ values are derived from log-probit analysis.

References

1. Snyder, S. H. and Coyle, J. T., "Regional differences in [$^3$H]-dopamine uptake into rat brain homogenates." J. Pharmacol. Exp. Ther. 165: 78–86 (1969).
2. Holz, R. W. and Coyle, J. T., "The effects of various salts, temperature and the alkaloids veratridine and batrachotoxin on the uptake of [$^3$H]-dopamine into synaptosomes from rat brain." Mol. Pharmacol. 10: 746–758 (1974).
3. Horn, A. S., Coyle, J. T. and Snyder, S. H., "Catecholamine uptake by synaptosomes from rat brain: Structure-activity relationships of drugs with differential effects on dopamine and norepinephrine neurons." Mol. Pharmacol. 7: 66–80 (1970).
4. Hunt, R., Raynaud, J. P., Leven, M. and Schacht, U., "Dopamine uptake inhibitors and releasing agents differentiated by the use of synaptosomes and field stimulated brain slices." Biochem. Pharmacol. 28: 2011–2016 (1979).
5. Cooper, B. R., Hester, T. J. and Maxwell, R. A., "Behavioral and biochemical effects of the antidepressant bupropion (Wellbutrin): Evidence for selective blockage of dopamine uptake in vivo." J. Pharmacol. Exp. Ther. 215: 1127–134 (1980).
6. Coyle, J. T. and Snyder, S. H., "Catecholamine uptake by synaptosomes in homogenates of rat brain: Stereospecificity in different areas." J. Pharmacol. Exp. Ther. 170: 221–231 (1969).
7. Tuomisto, L., Tuomisto, J. and Smissman, E. E., "Dopamine uptake in striatal and hypothalamic synaptosomes: Conformational selectivity of the inhibition." Eur. J. Pharmacol. 25: 351–361 (1974). 8. Heikkila, R. E. Orlansky, H. and Cohen, G., "Studies on the distinction between uptake inhibition and release of [$^3$H]-dopamine in rat brain tissue slices." Biochem. Pharmacol. 24: 847–852 (1975).
9. Baumann, P. A. and Maitre, L., "Is drug inhibition of dopamine uptake a misinterpretation of in vitro experiments!" Nature 264: 789–790 (1976).
10. Raiteri, M., Angelini, F. and Levi, G., "A simple apparatus for studying the release of neurotransmitters from synaptosomes." Eur. J. Pharmacol. 25: 411–414 (1974).

TABLE I

| Compound | Whole brain synaptosomes % inhibition at 3.16 μmn | | |
|---|---|---|---|
| | NE | 5HT | DA |
| 2-(3-(4-[3-(4-chlorophenyl)-1,1-dioxo-3H-benzo[d]isothiazol-2-yl]piperidin-,1-yl)-propyl)isoindole-1,3-dione maleate | 28.37 | 29.02 | 57.36 |
| 2-(4-[3-(4-chlorophenyl)-1,1-dioxo-3H benzo[d]isothiazol-2-yl]piperidin-1-yl) ethylene maleate | 8.71 | 3.68 | 18.71 |
| 1-[4-(3-(4-[3-(4-chlorophenyl)-1,1-dioxo-3H-benzo[d]isothiazol-2-yl]-1-piperidin-1-yl)-propoxy-3-methoxyphenyl]-ethylene maleate | 55.23 | 48.78 | 67.94 |
| 3-(4-fluorophenyl)-2-(4-piperidinyl)-2,3-dihydrobenzo[d]isothiazole-1,1-dioxide hydrochloride | 25.02 | 37.92 | 30.34 |

Antidepressant activity is achieved when the compounds of the invention are administered to a subject requiring such treatment at an effective oral, parenteral or intravenous dose of from 0.1 to 50 mg/kg of body weight per day. A preferred effective dose within this range is from about 0.1 to 5 mg/kg of body weight per day.

A particularly preferred effective amount is about 1 mg/kg of body weight per day. It is to be understood, however, that for any particular subject, specific dosage regimens should be adjusted according to the individual need and the professional judgment of the person administering or supervising the administration of the compounds of the invention. It is to be further understood that the dosages set forth herein are examples only and that they do not, to any extent, limit the scope or practice of the invention.

Anti-Parkinson Disease activity is achieved when the compounds of the invention are administered to a subject requiring such treatment at an effective oral, parenteral or intravenous dose of from 0.1 to 50 mg/kg of body weight per day. A preferred effective dose within this range is from about 0.1 to 5 mg/kg of body weight per day. A particularly preferred effective amount is about 1 mg/kg of body weight per day. It is to be understood, however, that for any particular subject, specific dosage regimens should be adjusted according to the individual need and the professional judgment of the person administering or supervising the administration of the compounds of the invention. It is to be further understood that the dosages set forth herein are examples only and that they do not, to any extent, limit the scope or practice of the invention.

Effective amounts of the compounds of the present invention may be administered to a subject by one of various methods, for example, orally as in capsules is or tablets, parenterally in the form of sterile solutions or suspensions, and in some cases intravenously in the form of sterile solutions. The compounds of the invention, while effective themselves, may be formulated and administered in the form of their pharmaceutically acceptable acid solution salts for purposes of stability, convenience of crystallization, increased solubility and the like.

Preferred pharmaceutically acceptable acid addition salts include those derived from inorganic acids such as hydrochloric, hydrobromic, sulfuric, nitric, phosphoric. perchloric acids and the like as well as organic acids such as tartaric, citric, acetic, succinic, maleic, fumaric acids and the like.

The compounds of the present invention may be administered orally, for example, with an inert diluent or with an edible carrier. They may be enclosed in gelatin capsules or compressed into tablets. For the purpose of oral therapeutic administration, the compounds may be incorporated with excipients and used in the form of tablets, troches, capsules, elixirs, suspensions, syrups, wafers, chewing gums and the like. These preparations should contain at least 4% of the compounds of the invention, the active ingredient, but may be varied depending upon the particular form and may conveniently be between 4% to about 70% of the weight of the unit. The amount of the compound present in such compositions is such that a suitable dosage will be obtained. Preferred compositions and preparations according to the present invention are prepared so that an oral dosage form contains between 5.0–300 milligrams of the compounds of the invention.

The tablets, pills, capsules, troches and the like may also contain the following adjuvants: a binder such as microcrystalline cellulose, gum tragacanth or gelatin; an excipient such as starch or lactose, a disintegrating agent such as alginic acid, Primogel, corn starch and the like; a lubricant such as magnesium stearate or Sterotex; a glidant such as colloidal silicon dioxide; and a sweetening agent such as sucrose or saccharin may be added or a flavoring agent such as peppermint, methyl salicylate or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus, tablets or pills may be coated with sugar, shellac, or other enteric coating agents. A syrup may contain, in addition to the present compounds, sucrose as a sweetening agent and certain preservatives, dyes and colorings and flavors. Materials used in preparing these various compositions should be pharmaceutically pure and non-toxic in the amounts used.

For the purpose of parenteral therapeutic administration, the compounds of the present invention may be incorporated into a solution or suspension. These preparations should contain at least 0.1% of the compounds of the invention, but may be varied to be between 0.1 and about 50% of the weight thereof. The amount of the inventive compound present in such compositions is such that a suitable dosage will be obtained. Preferred compositions and preparations according to the present invention are prepared so that a parenteral dosage unit contains between 5.0 to 100 milligrams of the compounds of the invention.

The solutions or suspensions may also include the following adjuvants: a sterile diluent such as water for injection, saline solution, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as ethylene diaminetetraacetic acid; buffers such as acetates, citrates or phosphates and agents for the adjustment of tonicity such as sodium chloride or dextrose. The parenteral preparation can be enclosed in ampules, disposable syringes or multiple dose vials made of glass or plastic.

The following examples are presented in order to illustrate this invention, in Table 2, typical compounds of the invention are listed. Following Table 2, representative illustrative preparations of compounds of the invention are described.

TABLE 2

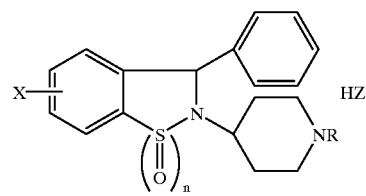

| # | X | Y | R | n | HZ | m.p. ° C. |
|---|---|---|---|---|----|-----------|
| 2 | H | 4-Cl | $CH_2C_6H_5$ | 2 | | 174–175 |
| 3 | H | 4-Cl | H | 2 | HCl 0.5$H_2$O | 72–85 |
| 4 | H | 4-Cl | —$CH_2CH_2OH$ | 2 | $C_4H_4OH$ | 182–184 |

TABLE 2-continued

| # | X | Y | R | n | HZ | m.p. ° C. |
|---|---|---|---|---|---|---|
| 5 | H | 4-Cl | —(CH₂)₃—phthalimide | 2 | C₄H₄O₄ | 191–192 |
| 6 | H | 4-Cl | —(CH₂)₃—phthalimide | 2 | C₄H₄O₄ | 189–191 |
| 7 | H | 4-Cl | —(CH₂)₃—O—(3-methoxy-4-acetylphenyl) | 2 | C₄H₄O₄ | 141–145 |
| 8 | H | 4-F | —CH₂—C₆H₅ | 2 | H | 118–119 |
| 9 | H | 4-F | H | 2 | HCl | 271–272 |

EXAMPLE 1 N-(1-benzylpiperidin-4-yl)-benzenesulfonamide

To a solution of 10.0 g, 52.6 mmol, of 4-amino-1-benzylpiperidine in 150 ml of dichloromethane was added 1.36 g (53 mmol) of benzene sulfonylchloride. The solution was stirred for 1 hour at room temperature, diluted with 500 mL of dichloromethane and washed with 5% aqueous sodium hydroxide followed by water and brine. The organic phase was separated, dried (MgSO₄), and concentrated in vacuo to give 16.6 g of product as an oil. The compound was used without further purification.

EXAMPLE 2 2-(1-Benzylpiperidin-4-yl)-3-(4-chlorophenyl)-2,3-dihydrobenzo[d]-isothiazole-1,1-dioxide To a solution of 19.16 g (58.1 mmol) of N-(1-benzylpiperidin-4-yl)-benzene sulfonamide in 300 mL of dimethoxyethane at 0° C. was added 46.4 mL (116.1 mmol) of a n-butyllithium (2.5 M) slowly via addition funnel. The mixture was stirred using an overhead stirrer for 45 minutes at 0° C., then 9.61 g (63.9 mmol) of p-chlorobenzaldehyde was added in one portion. The mixture was allowed to warm to room temperature, diluted with 1 liter of ethylacetate and washed 2×500 mL of water followed by 500 mL of brine. The organic phase was separated, dried (MgSO₄), and concentrated in vacuo. The residue was flash chromatographed over 300 g of silica gel (eluted with ethylacetate:heptane–2:1) to afford 17.3 g of product as an orange paste.

The aforementioned residue was dissolved in 40 mL of concentrated sulfuric acid at room temperature and stirred for 2 hours. The mixture was poured onto ice and the solid precipitate was collected. The precipitate was partitioned between 200 mL of 5% aqueous sodium hydroxide and 250 mL of ethylacetate. The organic phase was washed (2×200 mL) of water followed by 200 mL of brine. The organic phase was separated, dried (MgSO₄) and concentrated in vacuo. The residue was flash chromatographed over 200 g of silica gel (eluted with ethylacetate:heptane–1:1) to afford 7.42 g (28%) of a white solid, m.p. 174–175° C.

EXAMPLE 3 3-(4-Chlorophenyl)-2-(4-piperidinyl)-2,3-dihydrobenzo[d]-isothiazole-1,1-dioxide-hydrochloride hemihydrate To a solution of 2-(1-benzylpiperidin-4-yl)-3-(4-chlorophenyl)-2,3-dihydrobenzo-[d]isothiazole-1,1-dioxide (7.25 g, 16 mmol), of Example 6(a), in 50 ml dichloroethane at 0° C. under nitrogen was added chloroethyl chloroformate (1.9 ml, 17.6 mmol). The reaction was stirred for 5 minutes, then for 30 minutes allowing it to warm to room temperature, and concentrated in vacuo at 300° C., followed by flash chromatography over silica gel eluting with heptane:ethylene acetate (1:1). The intermediate obtained was heated in methanol for 10 minutes, chilled, and filtered to afford 5.35 g (84% yield) of a solid. This was combined with 4.1 g from a similar preparation and recrystallized from CH₂Cl₂ to give 9.0 g (77.5% yield) of product as the hydrochloride, m.p. >285° C.

ANALYSIS:
Calculated for $C_{18}H_{19}ClN_2O_2S \cdot HCl \cdot 0.5H_2O$: 52.95% C 5.18% H 6.86% N
Found: 53.26% C 5.20% H 6.82% N

EXAMPLE 4 2-{4-[3(4-Chlorophenyl)-1,1-dioxo-3H-benzo[d]isothiazol-2-yl]-piperidin-1-yl}-ethanol maleate To a solution of 2.0 g (5.01 mmol) of 3-(4-chlorophenyl)-2-(4-piperidin-yl)-2,3-dihydro-benzo[d]isothiazol-1,1-dioxide hydrochloride hemihydrate [Example 1(a)] in 20 mL of dimethylformamide was added 930 mg (7.5 mmol) of 2-bromoethanol followed by 2.7 g (20.0 mmol) of potassium carbonate. The mixture was warmed under reflux for 12 hours, allowed to cool to room temperature, diluted with ethyl acetate and washed with water. The organic phase was separated, dried ($MgSO_4$), and concentrated in vacuo. The residue was flash chromatographed over silica gel [(eluted with $CHCl_3$:MeOH=1:6)] to afford 823 mg of the amino alcohol as a solid.

To a solution of the free amine in 20 mL of dichloromethane was added 235 mg (2.03 mmol) of maleic acid. The solution was concentrated in vacuo and crystallized from ethyl acetate to give 980 mg (37%) of the maleate salt as a solid, m.p. 182–184° C.
ANALYSIS:
Calculated for $C_{20}H_{23}ClN_2O_3S \cdot C_4H_4O_4$: 55.12% C 5.20% H 5.36% N
Found: 54.97% C 4.94% H 5.24% N

EXAMPLE 5 2-(3-{4-[3-(4-Chlorophenyl)-1,1-dioxo-3H-benzo[d]isothiazol-2-yl]piperidin-1-yl}propyl)-isoindol-1,3-dione maleate To a solution of 2.30 g (5.76 mmol) of 3-(4-chlorophenyl)-2-(4-piperidin-yl)-2,3-dihydro-benzo[d]isothiazol-1,1-dioxide hydrochloride hemihydrate in 10 mL of dimethylformamide was added 1.70 g (6.34 mmol) of N-(3-bromopropyl)-phthalimide followed by 2.38 g (17.28 mmol) of potassium carbonate. The solution was warmed to 100° C. and stirred over night. The solution was allowed to cool to room temperature, diluted with 200 mL of ethyl acetate and washed with water. The organic phase was separated, dried ($MgSO_4$), and concentrated. The residue was flash chromatographed over silica gel (eluted with ethyl acetate) to afford 1.93 g of an oily-solid. The residue was dissolved in 10 mL of ethyl acetate and 0.5 mL of concentrated hydrochloric acid was added. The mixture was concentrated in vacuo and dissolved in a minimum amount of dichloromethane. The hydrochloride salt was precipitated with diethyl ether to give 2.34 g (69%) of product as a solid.

A solution of 1.77 g (3.0 mmol) of the hydrochloride salt in 200 mL of ethyl acetate was washed with 200 mL of 5% aqueous sodium hydroxide followed by 200 mL of water and 200 mL of brine. The organic phase was separated, dried ($MgSO_4$), and concentrated in vacuo. To a solution of the residue in 20 mL of ethyl acetate was added 371 mg (3.2 mmol) of maleic acid. The mixture was warmed then concentrated in vacuo. The residue was recrystallized from dichloromethane:cyclohexane (1:10) to afford 1.95 g (97%) of the maleate salt as a solid, m.p. 191–192° C.
ANALYSIS
Calculated for $C_{33}H_{32}ClN_3O_8S$: 59.50% C 4.84% H 6.15% N
Found: 59.22% C 4.57% H 6.15% N

EXAMPLE 6 2-(2-{4-[3-(4-Chlorophenyl)-1,1-dioxo-3H-benzo[d]isothiazol-2-yl]piperidin-1-yl}propyl)-isoindol-1,3-dione maleate To a solution of 2.00 g (5.0 mmol) of 3-(4-chlorophenyl)-2-(4-piperidinyl)-2,3-dihydro-benzo[d]isothiazol-1,1-dioxide hydrochloride of Example 6(b) in 20 mL of dimethylformamide was added of N-(2-bromomethyl)-phthalmide (1.5 g, 6.0 mmol) followed by potassium carbonate (2.1 g, 15 mmol). The solution was stirred and heated at 100° C. for 2 hours. The solution was allowed to cool to room temperature, diluted with 200 ml of ethyl acetate and washed with water and brine. The organic phase was separated, dried ($MgSO_4$), and concentrated in vacuo. The residue was flash chromatographed over silica gel [(eluted with ethyl acetate:heptane 1:1)] to afford 1.05 g of an oil. This was dissolved in 20 mL of ethyl acetate, and 1 equivalent of maleic acid was added. The mixture was concentrated in vacuo and recrystallized twice from ethyl acetate to give 0.48 g (15% yield) of the maleate salt as a solid, m.p.=189–191° C.
ANALYSIS:
Calculated for $C_{28}H_{26}ClN_3O_4S \cdot C_4H_4O_7$: 58.94% C 4.64% H 6.44% N
Found: 58.85% C 4.65% H 6.31% N

EXAMPLE 7 1-[4-(3-{4-[3-(4-Chlorophenyl)-1,1-dioxo-3H-benzo[d]isothiazol-2-yl]-1-piperidin-1-yl}-propoxy)-3-methoxyphenyl]-ethanone maleate To a solution of 2.0 g (5.0 mmol) of 3-(4-chlorophenyl)-2-piperidin-4-yl-2,3-dihydro-benzo[d]isothiazol-1,1-dioxide hydrochloride of Example 1(a) in 15 mL of dimethylformamide was added 1.24 g (5.1 mmol) of 4(3-chloropropoxy)-3-methoxy acetophenone, followed by 2.0 g (15 mmol) of potassium carbonate. The mixture was warmed under reflux for 15 hours, allowed to cool to room temperature, and diluted with 100 mL of ethyl acetate. The organic phase was washed with water followed by brine. The organic phase was separated, dried ($MgSO_4$), and concentrated in vacuo. The residue was flash chromatographed over silica gel (eluted with ethyl acetate) to afford 2.10 g of the product as a paste.

To a solution of the free amine in 20 mL of ethyl acetate was added 425 mg (3.89 mmol) of maleic acid. The solution was stirred for 10 minutes with gentle warming. The solution was cooled to 0° C. and the maleate salt was precipitated to afford 2.34 g of a solid. The solid was recrystallized from ethyl acetate to give 1.62 g (47%) of the product as a solid, m.p.=141–145° C.
ANALYSIS:
Calculated for $C_{30}H_{33}ClN_2O_5S \cdot C_4H_4O_4$: 59.60% C 5.44% H 4.09% N
Found: 59.53% C 5.45% H 3.99% N

EXAMPLE 8 2-(1-Benzylpiperidin-4-yl)-3-(4-fluorophenyl)-2,3-dihydrobenzo[d]-isothiazole-1,1-dioxide A solution of N-(1-benzylpiperidin-4-yl) benzenesulfonamide from Example 1 above, (18.7 g, 56.5 mmol) and 210 ml dimethoxyethane was chilled at 0° C. under $N_2$, followed by a slow addition over 25 minutes of 2.3 equivalent of n-butyl lithium (52 ml, 2.5 N/hexanes, 130 mmol) keeping the temperature below 15° C. After mechanically stirring for 35 minutes longer, 4-fluorobenzaldehyde (7.4 g, 59 mmol) in 50 ml dimethoxyethane was added at 5° C., and the reaction was stirred for 2 hours. Ether (400 ml) was added, and the reaction was washed with water and brine, dried ($MgSO_4$), and concentrated in vacuo. The residue was chromatographed on silica gel eluting with $CHCl_3$ to $CHCl_3$:5% MeOH to afford 11.85 g (46% yield) of the intermediate as a foam.

Most of the intermediate (10.85 g) was stirred until dissolved in 35 ml of concentrated sulfuric acid for 2 hours, then poured onto ice, and the resulting solid was filtered. The solid was partitioned between ethyl acetate and 5% NaOH until pH 10, and the organic layer was dried (MgSO$_4$), and concentrated in vacuo. This was purified on silica gel eluting with CHCl$_3$:1% methanol, and then recrystallized from ether to give 4.9 g (24% yield) of product as a solid, m.p.=118–119° C.
ANALYSIS:
Calculated for C$_{25}$H$_{25}$FN$_2$O$_2$S: 68.78% C 5.77% H 6.42% N
Found: 68.75% C 5.67% H 6.37% N

EXAMPLE 9 3-(4-Fluorophenyl)-2-(4-piperidinyl)-2,3-dihydrobenzo[d]isothiazole-1,1-dioxide hydrochloride To a solution of 2-(1-benzylpiperidin-4-yl)-3-(4-fluorophenyl)-2,3-dihydrobenzo-[d]isothiazole-1,1-dioxide (8.5 g, 19.4 mmol) of Example 8 in 80 m dichloroethane at 5° C. under nitrogen was added chloroethyl chloroformate (2.3 ml, 21.4 mmol). The reaction was stirred for 1 hour allowing it to warm to room temperature, and then concentrated in vacuo at 30–35° C. to an oil which was flash chromatographed over silica gel eluting with CHCl$_3$ to CHCl$_3$ to CHCl$_3$:2% methanol. The intermediate obtained was heated in methanol for 1 hour, evaporated, and slurried with ethyl acetate to afford 5.4 g (72% yield) of a solid. This was recrystallized from methanol to give 3.4 g (45.5% yield) of product as the hydrochloride, m.p.-271–272° C.
ANALYSIS:
Calculated for C$_{18}$H$_{19}$FN$_2$O$_2$SHCl: 56.47% C 5.27% H 7.32% N
Found: 56.28% C 5.13% H 7.16% N

We claim:

1. A compound having the formula

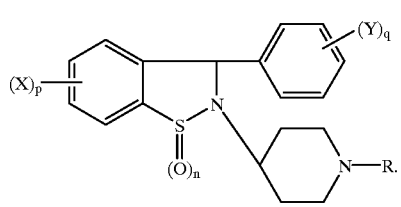

where X and Y are independently halogen, loweralkyl, loweralkoxy, arylloweralkoxy, where aryl has the formula

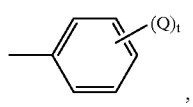

where Q is hydrogen, halogen, nitro, loweralkyl, loweralkoxy, loweracyl of the formula —C(=O)R$_2$ where R$_2$ is aryl, as previously defined, or loweralkyl, and t is an integer of 1 to 3; acyl, as previously defined, hydroxy, nitro, amino, trifluoromethyl and hydrogen;

n, p and q are independently integers of 1 or 2; 1

R is hydrogen, loweralkyl, arylloweralkyl, of the formula-alkylene

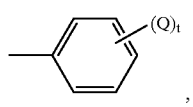

where alkylene is a bivalent radical of a lower branched or unbranched alkyl group of 1 to 6 carbon atoms and Q and t are as previously defined; acyl, as previously defined —(CH$_2$)$_m$—OR$_1$,—(CH$_2$)NHR$_1$,

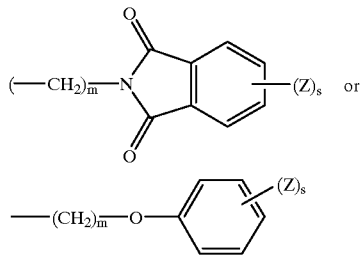

where R$_1$ is hydrogen, loweralkyl, arylloweralkyl, as previously defined, acyl as previously defined or loweralkoxycarbonyl;

Z is hydrogen, halogen loweralkyl, loweralkoxy or acyl, as previously defined;

m is an integer of 2 to 4;

s is an integer of 1 or 2; and a pharmaceutically acceptable acid addition salt thereof or an optical isomer thereof where such isomer exists.

2. The compound as defined in claim 1 wherein R is arylloweralkyl, acyl, —(CH)$_m$—OR$_1$, or —(CH$_2$)NHR$_1$.

3. The compound as defined in claim 1 wherein R is

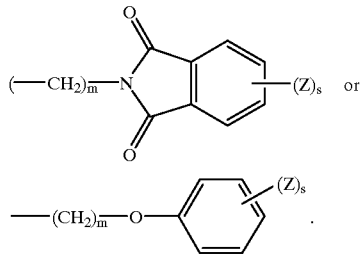

.

4. The compound as defined in claim 1 which is 2-(3-[4-[3-(4-chlorophenyl)-1,1-dioxo-3H-benzo[d]isothiazol-2-yl]piperidin-1-yl]propyl)-isoindole-1,3-dione or a pharmaceutically acceptable salt thereof.

5. The compound as defined in claim 4 wherein said salt is maleate.

6. The compound as defined in claim 1 which is 2-[4-[3-(4-chlorophenyl)-1,1-dioxo-3H-benzo[d]isothiazol-2-yl]piperidin-1-yl)-ethanol or a pharmaceutically acceptable salt thereof.

7. The compound as defined in claim 6 wherein said salt is maleate.

8. The compound as defined in claim 1 which is 1-{4-[3-(4-chlorophenyl)-5 1,1-dioxo-3H-benzo[d]isothiazol-2-yl)-1-piperidin-1-yl}-propoxy-3-methoxyphenyl] ethanone or a pharmaceutically acceptable salt thereof.

9. The compound as defined in claim 8 wherein said salt is maleate.

10. The compound as defined in claim 1 which is 2-(1-benzylpiperidin-4-yl)-3-(4-fluorophenyl)-2,3-dihydrobenzo (d]isothiazole 1-1-dioxide or a pharmaceutically acceptable salt thereof.

11. The compound as defined in claim 1 which is 3-(4-fluorophenyl)-2-(4-piperidinyl)-2,3-dihydrobenzo[d]isothiazole 1,1-dioxide or a pharmaceutically acceptable salt thereof.

12. The compound as defined in claim 11 wherein said salt is hydrochloride.

13. The compound as defined in claim 1 which is 3-(4-chlorophenyl)-2-(4-5 piperidinyl)-2,3-dihydrobenzo[d]isothiazole-1,1-dioxide or a pharmaceutically acceptable salt thereof.

14. The compound as defined in claim 13, wherein said salt is hydrochloride hemihydrate.

15. The compound as defined in claim 1 which is 2-(2-{4-[3-(4-chlorophenyl)-1,1-dioxo-3H-benzo[d]isothiazol-2-yl]piperidin-1-yl}ethyl)isoindol-1,3 dione or a pharmaceutically acceptable salt thereof.

16. The compound as defined in claim 15 wherein said salt is maleate.

17. An antidepressant composition which comprises an effective antidepressant amount of a compound having the formula

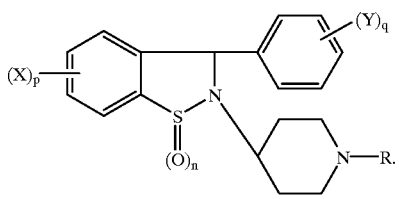

where X and Y are independently halogen, loweralkyl, loweralkoxy, arylloweralkoxy where aryl has the formula

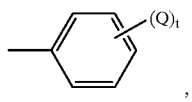

where Q is hydrogen, halogen, nitro, loweralkyl, loweralkoxy, loweracyl of the formula —C(=O)R$_2$, where R$_2$ is aryl, as previously defined, or loweralkyl, and t is an integer of 1 to 3; acyl, as previously defined, hydroxy, nitro, amino, trifluoromethyl or hydrogen;

n, p and q are independently integers of 1 or 2;

R is hydrogen, loweralkyl, aryloweralkyl of the formula-alkylene

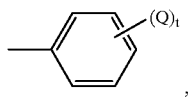

where alkylene is a bivalent radical of a lower branched or unbranched alkyl group of 1 to 6 carbon atoms and Q and t are as previously defined; acyl, as previously defined, —(CH$_2$)$_m$—OR$_1$, —(CH$_2$)NHR$_1$,

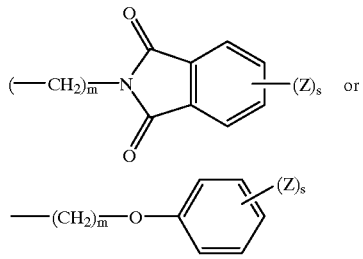

where R$_1$ is hydrogen, loweralkyl, arylloweralkyl as previously defined, acyl as previously defined or loweralkoxycarbonyl;

Z is hydrogen, halogen, loweralkyl, loweralkoxy or acyl as previously defined;

m is an integer of 2 to 4;

s is an integer of 1 or 2;

and a pharmaceutically acceptable acid addition salt thereof or an optical isomer thereof where such isomer exists.

18. The composition as defined in claim 17 wherein said R is hydrogen, loweralkyl and arylloweralkyl.

19. The composition as defined in claim 17 wherein said R is hydrogen, loweralkyl,

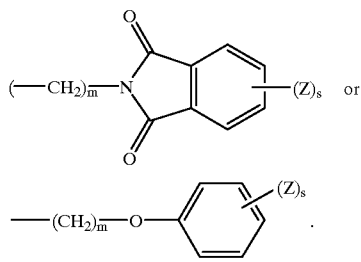

20. The composition as defined in claim 17 wherein said compound is 2-(3-[4-[3-(4-chlorophenyl)- 1,1-dioxo-3H-benzo[d]isothiazol-2-yl]piperidin- 1-yl]propyl)-isoindol-1,3-dione or a pharmaceutically acceptable salt thereof.

21. The composition as defined in claim 17 wherein said compound is maleate.

22. The composition as defined in claim 17 wherein said compound is 2-{4-[3-(4chlorophenyl)-1,1-dioxo-3H-benzo[d]isothiazol-2-yl)piperidin-1-yl)-ethanol or a pharmaceutically acceptable salt thereof.

23. The composition as defined in claim 17 wherein said salt is maleate.

24. The composition as defined in claim 17 wherein said compound is 1-{4-[3-(4-chlorophenyl)-1,1dioxo-3H-benzo[d]isothiazol-2-yl)- 1-piperidin- 1-yl} -propoxy-3-methoxyphenyl]-ethanone or a pharmaceutically acceptable salt thereof.

25. The composition as defined in claim 17 wherein said salt is maleate.

26. The composition as defined in claim 17 wherein said compound is 2-(1-benzylpiperidin-4-yl)-3-(4fluorophenyl)-2,3-dihydrobenzo[d]isothiazole-l-l-dioxide or a pharmaceutically acceptable salt thereof.

27. The composition as defined in claim 17 wherein said compound is 3-(4-fluorophenyl)-2-(4-piperidinyl)-2,3-dihydrobenzo[d]isothiazole-1,1-dioxide or a pharmaceutically acceptable salt thereof.

28. The composition as defined in claim 17 wherein said salt is maleate.

29. The composition as defined in claim 17 wherein said compound is 3-(4-chlorophenyl)-2-(4-piperidinyl)-2,3-dihydrobenzo[d]isothiazole-1,1-dioxide or a pharmaceutically acceptable salt thereof.

30. The composition as defined in claim 17 wherein said salt is hydrochloride hemihydrate.

31. The composition as defined in claim 17 wherein said compound is 2-(2-{4-[3-(4-chlorophenyl)-1,1dioxo-3H-benzo[d]isothiazol-2-yl]piperidin-1-yl}ethyl)isoindol-1,3 dione or a pharmaceutically acceptable salt thereof.

32. The composition as defined in claim 17 wherein said salt is a maleate.

33. A method of reducing depression in a patient in need thereof which comprises administering to a patient an effective antidepressant amount of a compound having the formula

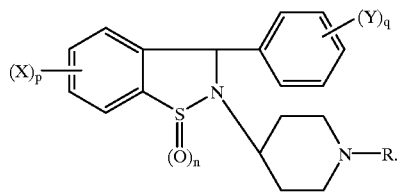

where X and Y are independently halogen, loweralkyl, loweralkoxy, arylloweralkoxy where aryl has the formula

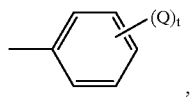

where Q is hydrogen, halogen, nitro, loweralkyl, loweralkoxy, loweracyl of the formula —C(=O)R$_2$ where R2 is aryl, as previously defined, or loweralkyl, and t is an integer of 1 to 3; acyl, as previously defined, acyl, hydroxy, nitro, amino, trifluoromethyl or hydrogen; where R$_1$ is hydrogen, loweralkyl, arylloweralkyl as previously defined, acyl as previously defined or loweralkoxycarbonyl;

Z is hydrogen, halogen, loweralkyl, loweralkoxy or acyl as previously defined;

m is an integer of 2 to 4;

s is an integer of 1 or 2; and a pharmaceutically acceptable acid addition salt thereof or an optical isomer thereof where such isomer exists.

34. The method as defined in claim 33 wherein R is arylloweralkyl, acyl, —(CH$_2$)$_m$—OR$_1$ or —(CH$_2$)NHR$_1$.

35. The method as defined in claim 33 wherein R is

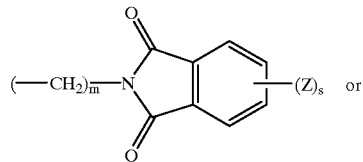 or

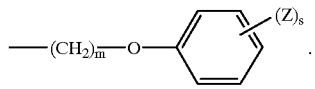.

36. The method as defined in claim 33 wherein said compound is 2-(3-[4-[3-(4-chlorophenyl)-1,1-dioxo-3H-benzo[d]isothiazol-2-yl]piperidin-1-yl]propyl)-isoindol-1,3-dione or a pharmaceutically acceptable salt thereof.

37. The method as defined in claim 33 wherein said salt is maleate.

38. The method as defined in claim 33 wherein said compound is 2-{4-[3-(4-chlorophenyl)-1,1-dioxo-3H-benzo[d]isothiazol-2-yl)piperidin-1-yl)-ethanol or a pharmaceutically acceptable salt thereof.

39. The method as defined in claim 33 wherein said salt is maleate.

40. The method as defined in claim 33 wherein said compound is 1-{4-[3-(4-chlorophenyl)-1,1-dioxo-3H-benzo[d]isothiazol-2-yl)- 1-piperidin-1-yl}-propoxy-3-methoxyphenyl]-ethanone or a pharmaceutically acceptable salt thereof.

41. The method as defined in claim 33 wherein said salt is maleate.

42. The method as defined in claim 33 wherein said compound is 2-(1-benzylpiperidin-4-yl)-3-(4-fluorophenyl)-2,3-dihydrobenzo[d]isothiazole-1-1-dioxide or a pharmaceutically acceptable salt thereof.

43. The method as defined in claim 33 wherein said compound is 3-(4-fluorophenyl)-2-(4-piperidinyl)-2,3-dihydrobenzo[d]isothiazole-1,)1,1-dioxide or a pharmaceutically acceptable salt thereof.

44. The method as defined in claim 33 wherein said salt is hydrochloride.

45. The method as defined in claim 33 wherein said compound is 3-(4-chlorophenyl)-2-(4-piperidinyl)-2,3-dihydrobenzo[d]isothiazole-1,1-dioxide or a pharmaceutically acceptable salt thereof.

46. The method as defined in claim 33 wherein said salt is hydrochloride hemihydrate.

47. The method as defined in claim 33 wherein said compound is 2-(2-{4-[3-(4-chlorophenyl)-1,1-dioxo-3H-benzo[d]isothiazol-2-yl]piperidin-1-yl}ethyl)isoindol-1,3 dione or a pharmaceutically acceptable salt thereof.

48. The method as defined in claim 33 wherein said salt is maleate.

* * * * *

UNITED STATES PATENT AND TRADEMARK OFFICE
CERTIFICATE OF CORRECTION

PATENT NO.    : 5,972,963
DATED         : October 26, 1999
INVENTOR(S)   : Gregory H. Merriman and Barbara S. Rauckman Page 1 of 1

It is certified that error appears in the above-identified patent and that said Letters Patent is hereby corrected as shown below:

<u>Column 17, claim 1,</u>
Line 57, which reads: "n, p and q are independently integers of 1 or 2; 1" should read -- "n, p and q are independently integers of 1 or 2; --

Signed and Sealed this

Nineteenth Day of March, 2002

Attest:

JAMES E. ROGAN
*Director of the United States Patent and Trademark Office*

*Attesting Officer*